United States Patent
Young et al.

(10) Patent No.: US 11,475,980 B2
(45) Date of Patent: *Oct. 18, 2022

(54) METHODS OF ANALYZING MASSIVELY PARALLEL SEQUENCING DATA

(71) Applicant: Battelle Memorial Institute, Columbus, OH (US)

(72) Inventors: Brian A. Young, Columbus, OH (US); Esley M. Heizer, Galloway, OH (US); Angela T. Minard-Smith, Marysville, OH (US); Nancy J. McMillan, Columbus, OH (US); Gokhan Yavas, Columbus, OH (US); Daniel M. Bornman, Powell, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 1340 days.

This patent is subject to a terminal disclaimer.

(21) Appl. No.: 14/489,198

(22) Filed: Sep. 17, 2014

(65) Prior Publication Data

US 2015/0032385 A1 Jan. 29, 2015

Related U.S. Application Data

(63) Continuation-in-part of application No. 13/952,761, filed on Jul. 29, 2013.

(51) Int. Cl.
G16B 30/00 (2019.01)

(52) U.S. Cl.
CPC .................... G16B 30/00 (2019.02)

(58) Field of Classification Search
None
See application file for complete search history.

(56) References Cited

PUBLICATIONS

Isaac Kinde, Jian Wu, Nick Papadopoulos, Kenneth W. Kinzler, and Bert Vogelstein, Detection and quantification of rare mutations with massively parallel sequencing, PNAS Jun. 7, 2011. 108 (23) 9530-9535; https://doi.org/10.1073/pnas.1105422108.*
ElizabethDay, Paul H.Dear, FrankMcCaughan , Review Article Digital PCR strategies in the development and analysis of molecular biomarkers for personalized medicine, Methods, vol. 59, Issue 1, Jan. 2013, pp. 101-107; https://doi.org/10.1016/j.ymeth.2012.08.001.*
Shendure et al nature biotechnology vol. 26 No. 10 Oct. 2008.*
Dollive et al., "A tool kit for quantifying eukaryotic rRNA gene sequences from human microbiome samples", http://genomebiology.com/2012/13/7/R60, 13 pages.
Gymrek et al., "lobSTR: A short tandem repeat profiler for personal genomes", downloaded from genome.cship.org on Sep. 22, 2015, 10 pages.
Gymrek et al., "Supplemental Material for lobSTR: A novel Pipeline for Short Tandem Repeats Profiling in Personal Genomes", 23 pages.
Warshauer et al., "STRait Razor: A length-based forensic STR allele-calling tool for use with second generation sequencing data", Forensic Science International: Genetics 7 (2013) 409-417.
Baum et al., Rapid Analysis of the Short Tandem Repeat HUMTH01 by Capillary Electrophoresis:, BioTechniques, vol. 17, No. 6 (1994), 6 pages.
Planz et al., "Automated analysis of sequence polymorphism in STR alleles by PCR and direct electrospray ionization mass spectrometry", Forensic Science International: Genetics 6 (2012) 594-606.
Schwartz et al., "AMPFLP-Typing of the D21S11 Microsatellite Polymorphism: Allele Frequencies and Sequencing Data in the Austrian Population", 16th Congress of the International Society for Forensic Haemogenetics (Internationale Gesellschaft für forensische Hämogenetik e.V.), Santiago de Compostela, Sep. 12-16, 1995, 4 pages.
Brinkmann et al., "Population Genetic Comparisons among Eight Populations using Allele Frequency and Sequence Data from Three Microsatellite Loci", Eur J Hum Genet 1996;4:175-182.
Zhou et al., "The HumD21S11 system of short tandem repeat DNA polymorphisms in Japanese and Chinese", Forensic Science International, 86 (1997) 109-118.
Griffiths et al., "New reference allelic ladders to improve allelic designation in a multiple STR system", Int J Legal Med (1998) 111:267-272.
Walsh et al., "Characterisation of variant alleles at the HumD21S11 locus implies unique Australasian genotypes and re-classification of nomenclature guidelines", Forensic Science International 135 (2003) 35-41.
Egyed et al., "Analysis of eith STR loci in two Hungarian populations", Forensic Science International 113 (2000) 25-27.
Schmitt et al., "Detection of ultra-rare mutations by next-generation sequencing", 14508-14513| PNAS| Sep. 4, 2012| vol. 109| No. 36.
Barber et al., "Sequenc analysis and allelic designation of the two short tandem repeat loci D18S51 and D8S1179", Int J Legal Med (1996) 109:62-65.
Walsh et al., "Sequence analysis and characterization of stutter products at the tetranucleotide repeat locus vWA", Nucleic Acids Research, 1996, vol. 24, No. 14 2807-2812.
Levinson et al., "Slipped-Strand Mispairing: A Major Mechanism for DNA Sequence Evolution", Mol. Biol. Evol. 4(3):203-221: 1987.

(Continued)

Primary Examiner — Joseph Woitach
(74) Attorney, Agent, or Firm — Barnes & Thornburg LLP

(57) ABSTRACT

In at least one illustrative embodiment, a method may comprise selecting a first plurality of text strings that each represent a nucleotide sequence that was read by a massively parallel sequencing instrument, where the nucleotide sequences represented by the selected first plurality of text strings each correspond to a first target locus, comparing the selected first plurality of text strings to one another to determine an abundance count for each unique text string included in the selected first plurality of text strings, identifying a first number of unique text strings included in the selected first plurality of text strings as representing noise responses, and determining a method detection limit as a function of the abundance counts for the first number of unique text strings identified as representing noise responses.

20 Claims, 7 Drawing Sheets

Specification includes a Sequence Listing.

(56) References Cited

PUBLICATIONS

Murray et al., "The determination of the sequences present in the shadow bands of a dinucleotide repeat PCR", Nucleic Acids Research, 1993, vol. 21, No. 10 2395-2398.

Hauge et al., "A study of the origin of 'shadow bands' seen when typing dinucleotide repeat polymorphisms by the PCR", Human Molecular Genetics, 1993, vol. 2, No. 4 411-415.

Schlotterer et al., "Slippage synthesis of simple sequence DNA", Nucleic Acids Research, vol. 20, No. 2 211-215.

Kircher et al., "Double indexing overcomes inaccuracies in multiple sequencing on the Illumina platform", Nucleic Acids Research, 2012, vol. 40, No. 1, 8 pages.

"DNA recommendations—further report of the DNA Commission of the ISFH regarding the use of short tandem repeat systems", Editorial, Forensic Science International 87 (1997) 179-184.

"Technical Focus, Definition of D19S433 in Life Technologies HID STR Products", Forensic News 2013, one page.

Moller et al., "Different types of structural vaiation in STRs: HumFES/FPS, HumVWA and HumD21S11", Int J Leg Med (1994) 106:319-323.

Cock et al., "The Sanger FASTQ file format for sequences with quality scores, and the Solexa/Illumina FASTQ variants", Nucleic Acids Research, 2010, vol. 38, No. 6, 1767-1771.

Sharma et al., "Spectral Repeat Finder (SRF): identification of repetitive sequences using Fourier transformation", Bioinformatics, vol. 20 No. 9, 2004, pp. 1405-1412.

Gary Benson, "Tandem repeats finder: a program to analyze DNA sequences", Nucleic Acids Research, 1999, vol. 27, No. 2, 573-580.

Sprecher et al., "General Approach to Analysis of Polymorphic Short Tandem Repeat Loci", BioTechniques, vol. 20, No. 2 (1996), 9 pages.

Butler et al., "Reliable genotyping of short tandem repeat loci without an allelic ladder using time-of-flight mass spectrometry", Int J Legal Med (1998) 112:45-49.

Fordyce et al., "Supplementary Material for: High-throughput sequencing of core STR loci for forensic genetic investigations using the Roche Genome Sequencer FLX platform", BioTechniques 51:127-133 (Aug. 2011).

Fordyce et al., "High-throughput sequencing of core STR loci for forensic genetic investigations using the Roche Genome Sequencer FLX platform", BioTechniques 51:127-133 (Aug. 2011).

Fondonm et al., "Analysis of Microsatellite Variation in *Drosophila melanogaster* with Population-Scale Genome Sequencing", PLos ONE, Mar. 2012, vol. 7, Issue 3, 9 pages.

Highnam et al., "Accurate human microsatellite genotypes from high-throughput resequencing data using informed error profiles", Nucleic Acids Research, 2013, vol. 41, No. 1, 7 pages.

Nielsen et al., "Genotype and SNP calling from next-generation sequencing data", Nature Reviews|Genetics, vol. 12, Jun. 2011, 9 pages.

"Microsatellite" downloaded from http://en.wikipedia.org/w/index.php?title=Microsatellite&oldid=5 Feb. 7, 2014, 13 pages.

Quail et al., A tale of three next generation sequencing platforms: comparison of Ion Torrent, Pacific Biosciences and Illumina MISeq sequencers:, BMIC Genomics 2012, 13:341, 13 pages.

Reiss et al., "The effect of replication errors on the mismatch analysis of PCR-amplified DNA", Nucleic Acids Research, vol. 18, No. 4, 6 pages.

Butler et al., "High-Throughput STR Analysis by Time-of-Flight Mass Spectrometry", pp. 121-130.

Bornman et al., "Short-read, high-throughput sequencing technology for STR genotyping", BioTechiques Rapid Dispatches, doi:10.21.44/000113857, 6 pages.

Gymrek et al., "lobSTR: A short tandem repeat profiler for personal genomes", downloaded from genome.cship.org on May 14, 2012, 10 pages.

Bizzaro et al., "Poly: a quantitative analysis tool for simple sequence repeat (SSR) tracts in DNA", BMC Bioinformatics 2003, 4:22, 6 pages.

Gilder et al., "Run-Specific Limits of Detection and Quantitation for STR-based DNA Testing", J Forensic Sci., Jan. 2007, vol. 52, No. 1, 5 pages.

Chen et al., "MfSAT: Detect simple sequence repeats in viral genomes", Bioinformation 6(4): 171-172 (2011).

International Search Report for PCT/US2014/027582, dated Jul. 11, 2014, 14 pages.

"Detection limit" downloaded from Wikipedia Oct. 14, 2015, 4 pages.

Catherine M. Grgicak, "Analytical Thresholds: Determination of Minimum Distinguishable Signals" ISHI 2010 Mixture Workshop, Oct. 11, 2010, 7 pages.

Van Neste et al., "My-Forensic-Loci-queries (MyFLq) framework for analysis of forensic STR data generated by massive parallel serquencing", Forensic Science International, Genetics 9 (2014) 1-8.

International Search Report for PCT/US2015/048082 dated Feb. 17, 2016, 17 pages.

Patent Trial and Appeal Board, Decision on Appeal for U.S. Appl. No. 13/834,830, Aug. 19, 2019, 22 pages.

Patent Trial and Appeal Board, Decision on Appeal for U.S. Appl. No. 13/952,761, Aug. 19, 2019, 13 pages.

\* cited by examiner

| SORT RANK | SEQUENCE | READ COUNT | ISFG SIZE | INTERPRETATION |
|---|---|---|---|---|
| 1 | [TCTA] [TCTG] 2 [TCTA] 12 | 82673 | 15 | TRUE ALLELE |
| 2 | [TCTA] [TCTG] 3 [TCTA] 12 | 56828 | 16 | TRUE ALLELE |
| 3 | [TCTA] [TCTG] 2 [TCTA] 11 | 6760 | 14 | -1 STUTTER |
| 4 | [TCTA] [TCTG] 3 [TCTA] 11 | 5047 | 15 | -1 STUTTER |
| 5 | [TCTA] [TCTG] 2 [TCTA] 13 | 974 | 16 | +1 STUTTER |
| 6 | [TCTA] [TCTG] [TCTA] 13 | 521 | 15 | SEQUENCE ERROR |
| 7 | [TCTA] [TCTG] 2 [TCTA] 10 | 465 | 13 | SEQUENCE ERROR |
| 8 | [TCTA] [TCTG] 2 [TCTA] 2CCTA [TCTA] 9 | 366 | 15 | SEQUENCE ERROR |
| 9 | [TCTA] [TCTG] 2 [TCTA] 7 CCTA[TCTA] 4 | 296 | 15 | SEQUENCE ERROR |
| 10 | [TCTA] [TCTG] 2 [TCTA] 3 [TCTG] [TCTA] 8 | 283 | 15 | SEQUENCE ERROR |
| ... | ... | ... | ... | ... |
| 2099 | CCTAGCTG [TCTG] 2 [TCTA] 12 | 1 | 16 | SEQUENCE ERROR |
| 2100 | CCTAACTG [TCTG] 2 [TCTA] 12 | 1 | 16 | SEQUENCE ERROR |
| 2101 | ACTA [TCTG] 2TTTA [TCTA] 6TTTA [TCTA] 4 | 1 | 15 | SEQUENCE ERROR |
| 2102 | ACTA [TCTG] 3 [TCTA] 10CCTA [TCTA] | 1 | 16 | SEQUENCE ERROR |
| 2103 | ACTA [TCTG] 2 [TCTA] 2 [TCTG] [TCTA] 9 | 1 | 15 | SEQUENCE ERROR |
| 2104 | ACTA [TCTG] 2 [TCTA] 11 | 1 | 14 | SEQUENCE ERROR |
| 2105 | ACTA [TCTG] 2 [TCTA] 10ACTA [TCTA] | 1 | 15 | SEQUENCE ERROR |
| 2106 | ACTA [TCTG] CCTG [TCTG] [TCTA] 12 | 1 | 16 | SEQUENCE ERROR |
| 2107 | ACTACCTG [TCTG] 2 [TCTA] 3TCCA [TCTA] 7 | 1 | 15 | SEQUENCE ERROR |
| 2108 | ACTAACTG [TCTG] [TCTA] 2TATA [TCTA] CCTATATA [TCTA] 6 | 1 | 15 | SEQUENCE ERROR |

FIG. 2

| LOCUS | SORT RANK | SEQUENCE | READ COUNT | LENGTH | INTERPRETATION |
|---|---|---|---|---|---|
| SAMPLE SRM2391C-A rs1805007 | 1 | C | 610 | 1 | TRUE ALLELE |
| | 2 | T | 3 | 1 | ERROR |
| | 3 | G | 1 | 1 | ERROR |
| | 4 | A | 0 | 1 | NA |
| SAMPLE SRM2391C-A rs16891982 | 1 | C | 283 | 1 | TRUE ALLELE |
| | 2 | G | 271 | 1 | TRUE ALLELE |
| | 3 | T | 1 | 1 | ERROR |
| | 4 | A | 1 | 1 | ERROR |

FIG. 3

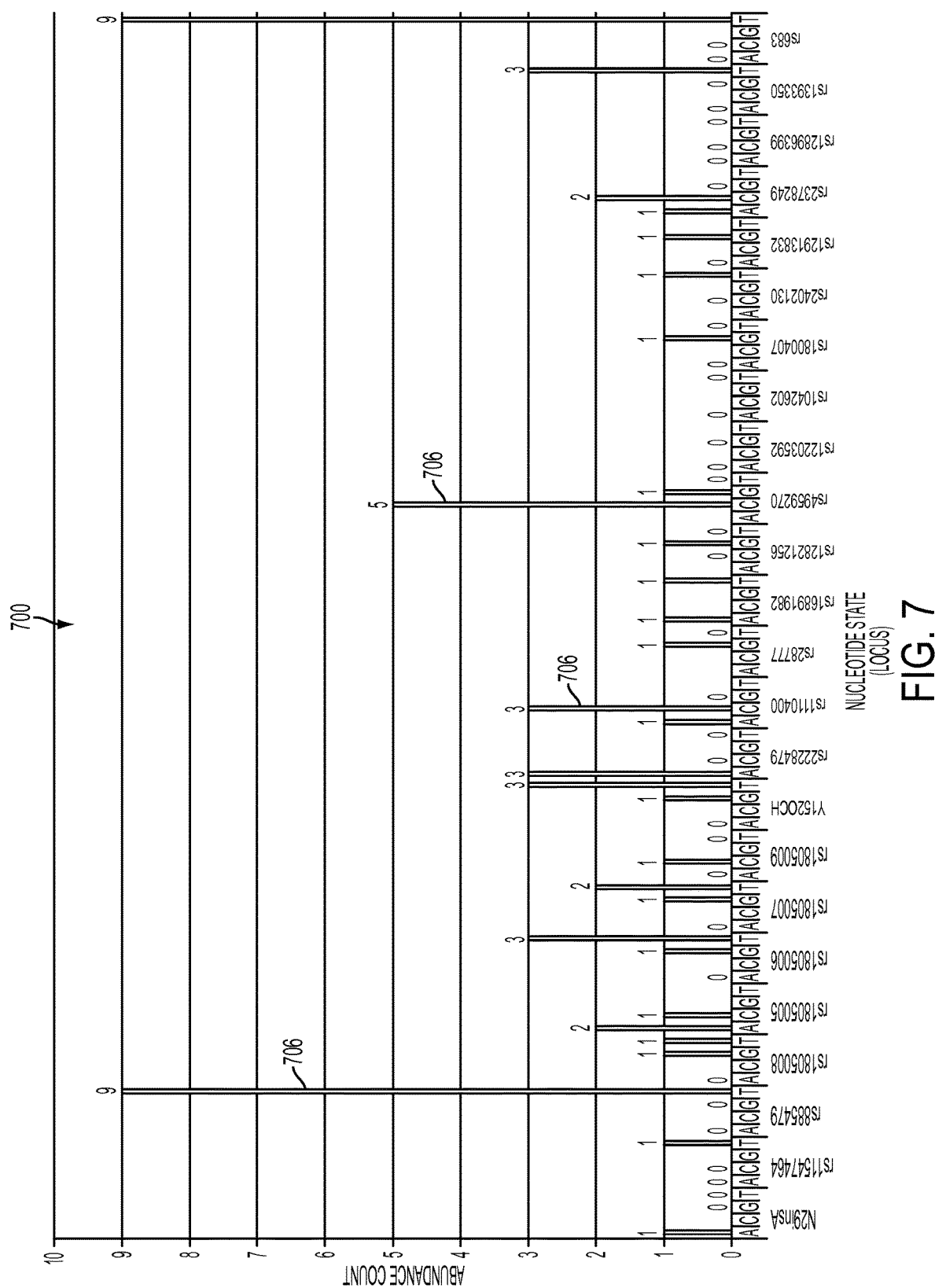

SEQUENCE LISTING

<160> NUMBER OF SEQ ID NOS: 20

<210> SEQ ID NO 1
<211> LENGTH: 60
<212> TYPE: DNA
<213> ORGANISM: Homo sapiens

<400> SEQUENCE: 1

```
tctatctgtc tgtctatcta tctatctatc tatctatcta tctatctatc tatctatcta    60
```

<210> SEQ ID NO 2
<211> LENGTH: 64
<212> TYPE: DNA
<213> ORGANISM: Homo sapiens

<400> SEQUENCE: 2

```
tctatctgtc tgtctgtcta tctatctatc tatctatcta tctatctatc tatctatcta    60
tcta                                                                 64
```

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
tctatctgtc tgtctatcta tctatctatc tatctatcta tctatctatc tatcta        56
```

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
tctatctgtc tgtctgtcta tctatctatc tatctatcta tctatctatc tatctatcta    60
```

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
tctatctgtc tgtctatcta tctatctatc tatctatcta tctatctatc tatctatcta    60
tcta                                                                 64
```

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
tctatctgtc tatctatcta tctatctatc tatctatcta tctatctatc tatctatcta    60
```

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
tctatctgtc tgtctatcta tctatctatc tatctatcta tctatctatc ta            52
```

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
tctatctgtc tgtctatcta cctatctatc tatctatcta tctatctatc tatctatcta   60
```

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
tctatctgtc tgtctatcta tctatctatc tatctatcta cctatctatc tatctatcta   60
```

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
tctatctgtc tgtctatcta tctatctgtc tatctatcta tctatctatc tatctatcta   60
```

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
cctagctgtc tgtctgtcta tatctctatc tatctatcta tctatctatc tatctatcta   60
tcta                                                                 64
```

<210> SEQ ID NO 12
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
cctaactgtc tgtctgtcta tctatctatc tatctatcta tctatctatc tatctatcta   60
tcta                                                                 64
```

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
actatctgtc tgtttatcta tctatctatc tatctatcta tttatctatc tatctatcta        60

<210> SEQ ID NO 14
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
actatctgtc tgtctgtcta tctatctatc tatctatcta tctatctatc tatctaccta        60
tcta                                                                     64

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actatctgtc tgtctatcta tctgtctatc tatctatcta tctatctatc tatctatcta        60

<210> SEQ ID NO 16
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
actatctgtc tgtctatcta tctatctatc tatctatcta tctatctatc tatcta           56

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
actatctgtc tgtctatcta tctatctatc tatctatcta tctatctatc taactatcta        60

<210> SEQ ID NO 18
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
actatctgcc tgtctgtcta tctatctatc tatctatcta tctatctatc tatctatcta        60
tcta                                                                     64

<210> SEQ ID NO 19
<211> LENGTH: 60
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 19
actacctgtc tgtctgtcta tctatctatc catctatcta tctatctatc tatctatcta    60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
actaactgtc tgtctatcta tatatctacc tatatatcta tctatctatc tatctatcta    60
```

METHODS OF ANALYZING MASSIVELY PARALLEL SEQUENCING DATA

CROSS REFERENCE TO RELATED APPLICATION

This application is a continuation-in-part of U.S. patent application Ser. No. 13/952,761, filed Jul. 29, 2013 (entitled "Allelotyping Methods for Massively Parallel Sequencing"), the entire disclosure of which is incorporated by reference herein.

SEQUENCE LISTING

The instant application contains a Sequence Listing which has been submitted electronically in ASCII format and is hereby incorporated by reference in its entirety. The ASCII copy, created on Oct. 12, 2015, is named 920006-229539_SL.txt and is 5,376 bytes in size.

TECHNICAL FIELD

The present disclosure relates to methods of analyzing data derived from massively parallel sequencing (MPS), including methods of displaying data derived from MPS.

BACKGROUND

Polymorphic tandem repeats of nucleotide sequences are found throughout the human genome, and the particular combinations of alleles identified by their multiple repeat sites are sufficiently unique to an individual that these repeating sequences can be used in human or other organism identification. These markers are also useful in genetic mapping and linkage analysis, where the tandem repeat sites may be useful for determining, for example, predisposition for disease. Tandem repeats can be used directly in human identity testing, such as in forensics analysis. There are many types of tandem repeats of nucleic acids, falling under the general term variable number tandem repeats (VNTR). For example, minisatellites and microsatellites are VNTRs, and microsatellites include short tandem repeats (STRs).

One application of tandem repeat analysis is in forensics or human identity testing. In current forensics analyses, highly polymorphic STRs are identified using a deoxyribonucleic acid (DNA) sample from an individual and DNA amplification steps, such as polymerase chain reaction (PCR), to provide amplified samples of partial DNA sequences, or amplicons, from the individual's DNA. The amplicons can then be matched by size (i.e., repeat numbers) to reference databases, such as the sequences stored in national or local DNA databases. For example, amplicons that originate from STR loci can be matched to reference STR databases, including the Federal Bureau of Investigation (FBI) Combined DNA Index System (CODIS) database in the United States, or the National DNA Database (NDNAD) in the United Kingdom, to identify the individual by matching to the STR alleles specific to that individual.

Forensic DNA analysis is about to cross a threshold where DNA samples will begin to be analyzed routinely by MPS (also sometimes referred to in the art as "next-generation" or "current-generation" sequencing). The advent of routine MPS for forensic DNA analysis will create large quantities of nucleotide sequence data that may enable richer exploitation of DNA in forensic applications. Once information is generated on the genetic profile of an individual (e.g., for either forensic investigative purposes or confirmatory matching), the resulting nucleotide sequence data should be formatted for exchange among law enforcement entities. Data files created by MPS workflows can be larger than 1 gigaByte (GB), making them difficult to transmit or store. In addition, these files, while text-based, are not human-readable in any practical sense because of their large size. Thus, other human readable representations of the data from MPS workflows are needed.

SUMMARY

According to one aspect, a method may comprise selecting a first plurality of text strings that each represent a nucleotide sequence that was read by a massively parallel sequencing (MPS) instrument, wherein the nucleotide sequences represented by the selected first plurality of text strings each correspond to a first target locus, comparing the selected first plurality of text strings to one another to determine an abundance count for each unique text string included in the selected first plurality of text strings, identifying a first number of unique text strings included in the selected first plurality of text strings as representing noise responses, and determining a method detection limit (MDL) as a function of the abundance counts for the first number of unique text strings identified as representing noise responses.

In some embodiments, the method may further comprise identifying one or more unique text strings included in the selected first plurality of text strings as representing one or more true alleles for the first target locus. In such embodiments, the first number of unique text strings identified as representing noise responses may include all of the unique text strings included in the selected first plurality of text strings that were not identified as representing the one or more true alleles for the first target locus. Identifying one or more unique text strings as representing the one or more true alleles for the first target locus may comprise identifying a unique text string that represents either a short tandem repeat (STR) or a single nucleotide polymorphism (SNP).

In some embodiments, the method may further comprise identifying one or more unique text strings included in the selected first plurality of text strings as representing one or more true alleles for the first target locus and identifying one or more unique text strings included in the selected first plurality of text strings as each representing an artifact. In such embodiments, the first number of unique text strings identified as representing noise responses may include all of the unique text strings included in the selected first plurality of text strings that were not identified as representing either the one or more true alleles for the first target locus or an artifact. Identifying one or more unique text strings as representing the one or more true alleles for the first target locus may comprise identifying a unique text string that represents a short tandem repeat (STR), and identifying one or more unique text strings as representing an artifact comprises identifying a unique text string that represents a stutter artifact of the STR.

In some embodiments, determining the MDL may comprise doubling a difference between (i) a largest abundance count for the first number of unique text strings identified as representing noise responses and (ii) a smallest abundance count for the first number of unique text strings identified as representing noise responses. In other embodiments, determining the MDL comprises calculating a product of (i) a constant and (ii) a standard deviation of the abundance counts for the first number of unique text strings identified as representing noise responses. Determining the MDL may further comprise adding a mean of the abundance counts for the first number of unique text strings identified as representing noise responses to the product. In still other embodiments, determining the MDL may comprise calculating a ratio between (i) a mean of the abundance counts for the first number of unique text strings identified as representing noise responses and (ii) a standard deviation of the abundance counts for the first number of unique text strings identified as representing noise responses.

In some embodiments, the method may further comprise selecting a second plurality of text strings that each represent a nucleotide sequence that was read by the MPS instrument, wherein the nucleotide sequences represented by the selected second plurality of text strings each correspond to a second target locus, comparing the selected second plurality of text strings to one another to determine an abundance count for each unique text string included in the selected second plurality of text strings, and identifying a second number of unique text strings included in the selected second plurality of text strings as representing noise responses. In such embodiments, determining the MDL may comprise determining the MDL as a function of both the abundance counts for the first number of unique text strings identified as representing noise responses and the abundance counts for the second number of unique text strings identified as representing noise responses.

In some embodiments, the method may further comprise sequencing a sample using the MPS instrument to generate text strings that each represent a nucleotide sequence that was read by the MPS instrument. Selecting the first plurality of text strings for which the represented nucleotide sequences each correspond to the first target locus may comprise selecting the first plurality of text strings from among the text strings generated by the MPS instrument.

According to another aspect, a method may comprise selecting a first plurality of text strings that each represent a nucleotide sequence that was read by a massively parallel sequencing (MPS) instrument, wherein the nucleotide sequences represented by the selected first plurality of text strings each correspond to a first target locus, comparing the selected first plurality of text strings to one another to determine an abundance count for each unique text string included in the selected first plurality of text strings, and outputting a graphical display, wherein the graphical display comprises a first plurality of graphical elements that each correspond to one of the unique text strings included in the selected first plurality of text strings and that each represent the abundance count determined for the corresponding unique text string.

In some embodiments, the graphical display may be a bar graph comprising a plurality of bars that each correspond to one of the unique text strings included in the selected first plurality of text strings, each of the plurality of bars having a height indicative of the abundance count determined for the corresponding unique text string. The bar graph may further comprise a label associated with each of the plurality of bars, each label designating the nucleotide sequence represented by the corresponding unique text string. The plurality of bars may comprise one or more bars that each represent a true allele for the first target locus. The plurality of bars may be arranged in order of decreasing height. The plurality of bars may represent a full set of noise responses for the first target locus. The plurality of bars may be arranged in a random order.

In some embodiments, the method may further comprise selecting a second plurality of text strings that each represent a nucleotide sequence that was read by the MPS instrument, wherein the nucleotide sequences represented by the selected second plurality of text strings each correspond to a second target locus, and comparing the selected second plurality of text strings to one another to determine an abundance count for each unique text string included in the selected second plurality of text strings. In such embodiments, the graphical display may further comprise a second plurality of graphical elements that each correspond to one of the unique text strings included in the selected second plurality of text strings and that each represent the abundance count determined for the corresponding unique text string.

In some embodiments, the method may further comprise sequencing a sample using the MPS instrument to generate text strings that each represent a nucleotide sequence that was read by the MPS instrument. In such embodiments, selecting the first plurality of text strings for which the represented nucleotide sequences each correspond to the first target locus may comprise selecting the first plurality of text strings from among the text strings generated by the MPS instrument.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels may be repeated among the figures to indicate corresponding or analogous elements. The detailed description particularly refers to the accompanying figures in which:

FIG. 2 shows portions of an illustrative table including unique text strings that each represent a nucleotide sequence corresponding to a particular STR locus (namely, D3S1358) that was sequenced using MPS, where the unique text strings have been sorted by abundance (or "read") count (FIG. 2 discloses SEQ ID NOS 1-20, respectively, in order of appearance);

FIG. 3 shows an illustrative table including unique text strings (in this case, single text characters) that each represent a nucleotide sequence (in this case, a single nucleotide) corresponding to two particular single nucleotide polymorphism (SNP) loci (namely, rs1805007 and rs1681982) that were sequenced using MPS, where the unique text strings have been sorted by abundance (or "read") count;

FIG. 7 is still another illustrative embodiment of a kopiagram, representing the abundance counts of a full set of noise responses (in this case, excluding both true alleles and artifacts) obtained from MPS of twenty-four SNP loci of a sample.

DETAILED DESCRIPTION OF THE DRAWINGS

Figure 1:
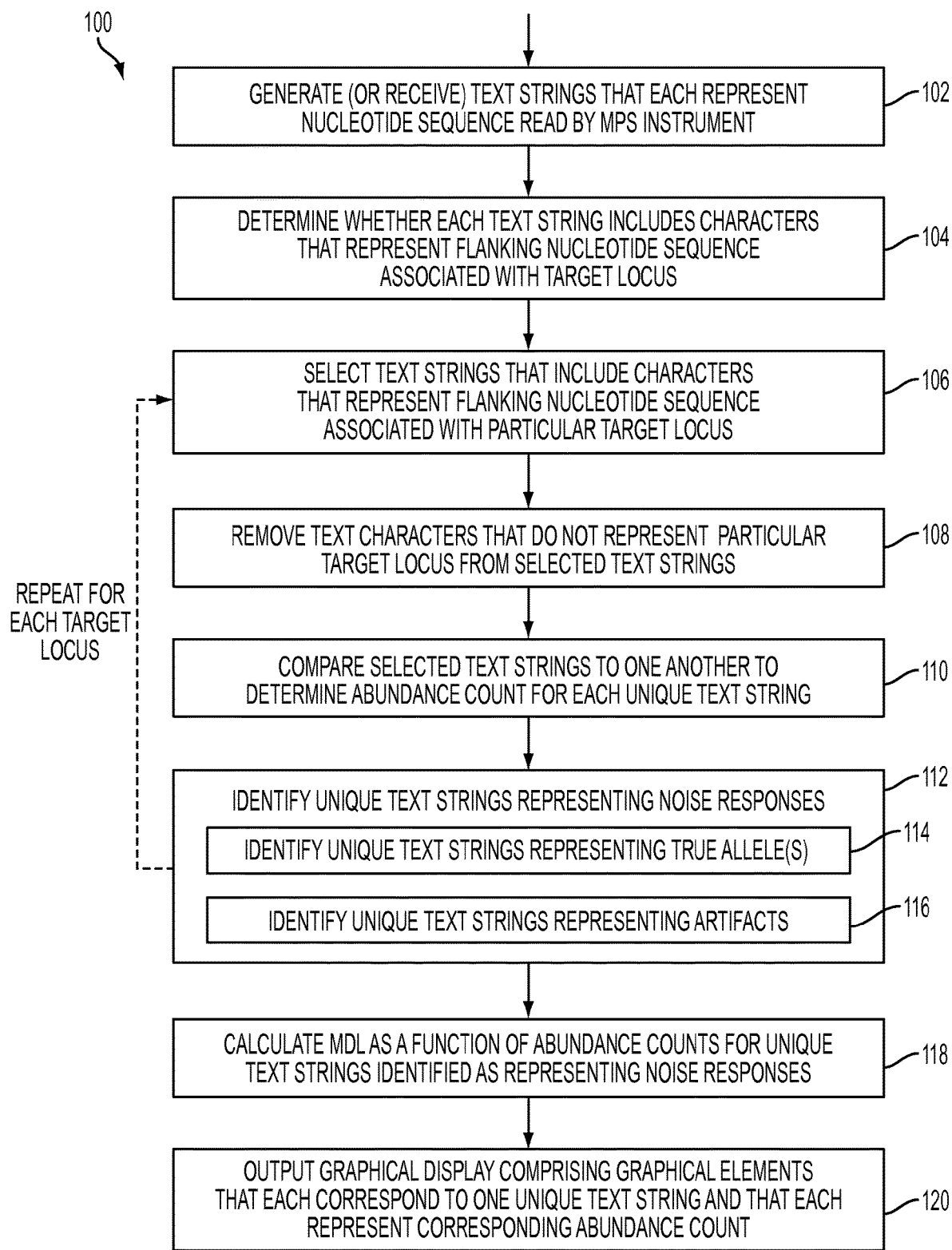
FIG. 1 is a simplified flow diagram illustrating one embodiment of a method of analyzing data derived from MPS.

While the concepts of the present disclosure are susceptible to various modifications and alternative forms, specific embodiments thereof have been shown by way of example in the figures and will be described herein in detail. It should be understood, however, that there is no intent to limit the concepts of the present disclosure to the particular forms disclosed, but to the contrary, the intention is to cover all modifications, equivalents, and alternatives consistent with the present disclosure and the appended claims.

References in the specification to "one embodiment," "an embodiment," "an illustrative embodiment," et cetera, indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The disclosed embodiments may be implemented, in some cases, in hardware, firmware, software, or any combination thereof. The disclosed embodiments may also be implemented as instructions carried by or stored on a transitory or non-transitory computer-readable storage medium, which may be read and executed by one or more processors. A computer-readable storage medium may be embodied as any storage device, mechanism, or other physical structure for storing or transmitting information in a form readable by a computing device (e.g., a volatile or non-volatile memory, a media disc, or other media device).

In the drawings, some features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

STR loci exist in multiple nucleotide sequence states, called alleles. Similarly, SNP loci exist in multiple single nucleotide states (usually two), which may also be called alleles. As used in the present disclosure, a "nucleotide sequence" may include one or more nucleotides. Alleles can be identical (as in homozygous conditions) or differ from one another by nucleotide sequence. In addition, STR alleles often differ from one another by sequence length (whereas the length of an SNP allele is always one, i.e., a single nucleotide). Allelotyping is the process of identifying the one or more "true" alleles present at one or more loci in a given sample (by way of example, for a sample from one human, the one "true" allele for each hemizygous locus, the two identical "true" alleles for each homozygous locus, or the two non-identical "true" alleles for each heterozygous locus). The FBI and other law enforcement agencies around the world have selected about twenty-four specific STR loci for use in forensic DNA analysis applications. These STR loci have been selected because they are highly polymorphic, i.e., multiple alleles exist within the relevant populations. For example, the thirteen STR loci considered by the FBI as their "core" loci each exhibit at least eight different common allelic forms.

A typical MPS process starts with a DNA sample, which is typically amplified using PCR (however, it will be appreciated that certain DNA samples can also be directly sequenced by MPS instruments without pre-amplification). The output of the MPS process typically takes the form of one or more computer files containing text strings representing the nucleotide sequences that were determined by the MPS instrument. The parallel nature of MPS results in numerous replicates of the nucleotide sequence of each allele. This is particularly true when the DNA is pre-amplified by PCR, where the number of replicates of each allelic sequence may number in the tens of thousands. However, both the PCR pre-amplification process and the sequencing process itself have non-trivial error rates.

Method errors are realized as incorrect nucleotide sequences in many of the copies of the original DNA sequences, i.e., the "true" alleles that existed in the original DNA sample. A first error type is the replacement of a correct nucleotide with an incorrect nucleotide (for example, where the MPS instrument incorrectly reads the nucleotide). A second error type is the erroneous insertion or deletion of one or more nucleotides. This second type of error is more common in DNA sequences where homopolymeric stretches of the same nucleotide occur. A third error type occurs when additional motifs in a tandem repeat sequence are inserted or deleted. This third type of error is more frequent in long stretches of tandem repeats than in shorter ones and occurs as a result of a strand-slippage mechanism during DNA polymerase replication as part of PCR amplification or during sequencing processes that employ DNA polymerase. Strand slippage error is commonly referred to as "stutter" in forensic science. While stutter is an error, in common forensic science practice, stutter is often differentiated from the instrumental noise baseline and is instead typically called an "artifact." Other artifacts, such as contamination from contributors other than the intended subject and instrument- or method-specific artifacts, are also possible. As described further below, such artifacts may optionally be considered (or not be considered) to be "noise" responses, depending on the particular embodiment of the present disclosure.

The diversity of unique nucleotide sequences generated by a PCR-MPS workflow can be illustrated using an experiment performed on a DNA sample from an anonymous human subject. This anonymous human subject was known to contain allele numbers 15 and 16 (with known sequences TCTA [TCTG]2 [TCTA] 12 (SEQ ID NO: 1) and TCTA [TCTG]3 [TCTA] 12 (SEQ ID NO: 2), respectively) at the D3S1358 locus. The MPS instrument returned approximately 130,000 replicate sequences for the two alleles at this locus (i.e., an average of 65,000 replicate sequences per allele). In the absence of error, only these two "true" allele nucleotide sequences would have been returned in the data generated by the MPS instrument. However, because of error in the PCR amplification and MPS processes, a total of 2108 unique nucleotide sequences were observed. Two correspond to the "true" alleles, while the remaining 2106 correspond to method artifacts and sequencing errors. FIG.

2 shows twenty of the 2108 unique nucleotide sequences output by the MPS instrument (the top ten most abundant nucleotide sequences and ten "singleton" nucleotide sequences that each occurred only once). In this case, the two most abundant unique nucleotide sequences correspond to the "true" alleles (particularly, allele numbers 15 and 16), and the next three most abundant unique nucleotide sequences correspond to PCR stutter artifacts (which may optionally be considered to be "noise" responses). The less abundant unique nucleotide sequences exhibit a wide range of mutations, including sequence truncations and base substitution errors, and are all considered to be "noise" responses.

To be useful in diagnostic applications, including medical diagnostics and forensic DNA analysis, an instrumental analysis method should have an objective method detection limit (MDL) above which responses representing meaningful information can be reliably discriminated from background noise responses. MDL generally refers to the detection limit based on the entire analytical method including sample preparation and instrumental analysis. An instrument detection limit (IDL) is a similar concept, but it is typically limited to considerations of the instrument/detector system. Another commonly used term in the art is level of detection (LOD), which is often used synonymously with both MDL and IDL. It will be appreciated that specific fields may use alternate terminology specific to their applications. For instance, in forensic DNA analysis, the MDL is often termed an analytical threshold (AT). While the present disclosure will generally refer to the determination of an MDL from MPS data, those of skill in the art will appreciate that the concepts of the present disclosure are also applicable to the determination of similar values, regardless of the specific terminology used.

Many methods for determining MDLs are based on ratios of informative signal to background noise. One such technique commonly used in instrumental analysis methods is based on repeated measurements of the same sample. The sample may contain target analyte (as in a positive control) or it may be absent of analyte (as in a negative control). When repeated measurements are made, noise may be expressed as a measure of variation in the measurements, usually the standard deviation of the repeated measurements. When analyte is present (as in positive controls), the signal may be expressed as the mean of the repeated measurements. Thus, a signal-to-noise ratio (S/N) may be calculated as the ratio of mean response ($\mu$) over the standard deviation ($\sigma$) of the responses:

$$S/N=\mu/\sigma \quad (1).$$

A repeated measurements approach may be assigned a confidence level using the recommended method of the U.S. Environmental Protection Agency (see 40 C.F.R., Part 136, Appendix B), where the alpha level is selected to achieve the desired confidence level:

$$MDL=t_{df,\alpha}*\sigma \quad (2).$$

By way of example, an alpha level of 0.1 may be selected for a 99% confidence level.

A method recommended by the International Conference on Harmonisation (ICH) determines MDLs from calibration curves for the target analyte or, alternatively, a simple dilution series of the target analyte. In this method, the MDL may be calculated based on the standard deviation of the Y-intercept of the calibration curves:

$$MDL=k*\sigma_b \quad (3),$$

where k is a constant (often 3) and $\sigma_b$ is the standard deviation of the intercept, based on a linear equation.

Repeated measurements-based noise estimation methods are broadly applicable and can be applied to virtually any analytical method or instrument system because virtually all methods and instrument systems experience background noise. Consequently, repeated measurements approaches to determining MDLs (such as those represented by Equations (1)-(3)) may be applied to instrumental analysis methods based on MPS of DNA. However, executing these methods through repeated measurements of the same sample(s) can add cost to the analysis. In contrast, methods for determining MDLs that utilize noise baseline measures (as described below) can be performed using existing positive or negative controls that are normally included with unknown samples as part of an overall laboratory quality control system (thus, avoiding the need for repeated measurements of the same sample(s)).

An instrument response baseline is an expression of noise responses as a function of a dependent variable, often time. The use of noise baselines facilitates the multiple measurements needed for calculating error variability, but without the need to re-analyze the same sample(s) multiple times. In noise baseline approaches, signal corresponds to instrument responses in time intervals where analyte responses are found, while background noise corresponds to instrument responses in time intervals where analyte responses are absent. Time intervals where signal is present may also contain noise, which is why the classical measure of signal corresponds to the mean of multiple measurements (thereby, averaging out noise variation). On the other hand, time intervals where signal is absent contain only noise.

One method recommended by ICH for calculating signal to noise ratios from systems with noise baselines uses the equation:

$$S/N=2H/h \quad (4),$$

where (i) H is the height of the peak measured from the peak apex to a baseline extrapolated over a distance greater than or equal to five times the peak width measured at its half-height and (ii) h is the difference between the largest and smallest noise values observed over a distance greater than or equal to five times the peak width measured at its half-height, if possible situated equally around the peak of interest. This method has particular application when the instrumental analysis involves chromatography or electrophoresis and a natural noise baseline is formed by formatting data along an axis that represents time (as in retention time) or distance (as in migration distance).

An alternative to Equation (4) is recommended by the FBI's Scientific Working Group on DNA Analysis Methods (SWGDAM) where the MDL is determined by taking twice the amplitude difference between the highest peak and the lowest valley in the noise baseline:

$$MDL=2(Y_{max}-Y_{min}) \quad (5).$$

Another alternative is recommended by manufacturers of reagents that are used in forensic DNA analysis methods based on PCR fragment analysis using capillary-electrophoresis (CE) instrumental detection. In this approach, electropherograms of positive control samples are examined, and time windows which are absent of analyte (amplified DNA) or method artifacts are selected. The mean ($\mu$) and standard deviation ($\sigma$) are calculated for the noise peak heights in the selected time windows. The following equation may then be used to calculate the MDL, with the value of k selected to achieve the desired confidence level:

$$MDL = \mu + k^*\sigma \quad (6).$$

By way of example, assuming the noise peaks exhibit a Gaussian distribution, a k value of 3 will result in a 99.7% confidence interval.

MPS data are of a different form and format from the data generated by current standard forensic DNA analysis techniques for STR, SNP, and mitochondrial DNA (mtDNA) markers. In the case of current STR analysis techniques, the various alleles are discriminated using CE, with alleles of different sizes exhibiting differential electrophoretic retention times. As discussed above, the time windows in electropherograms where signal and artifacts are absent, present natural noise baselines useful for analysis. Alternatively, STR alleles can be sequenced using previous-generation Sanger sequencing, described further below. Current SNP analysis techniques include PCR-based methods, DNA microarray-based methods, and sequencing-based methods (such as previous-generation Sanger sequencing). PCR- and microarray-based methods of analyzing SNP markers produce data forms that can be analyzed for background noise using repeated measures methods. However, neither of these methods produces a usable dimension-dependent (e.g., time-dependent or distance-dependent) noise baseline. Current mtDNA analysis techniques rely primarily on previous-generation Sanger sequencing.

The previous-generation Sanger sequencing method is a time-dependent process and, therefore, the data produced by this method includes a noise baseline suitable for noise-baseline-based analyses. The Sanger sequencing process uses CE through which DNA sequences are deciphered one nucleotide at a time as detected by retention time differences of one-nucleotide different DNA fragments. The noise baseline is clearly observable in Sanger sequencing electropherograms as minor fluorescence responses underlying the fluorescence responses of the analytes (DNA fragments). Pure noise baselines in the absence of signal are also available in time windows where target analyte is not present.

The low-level raw data generated by MPS instruments does have a time dimension in fluorescence or hydrogen ion detection (depending upon the particular sequencing technology used by the MPS instrument). On-board software in MPS instruments typically performs primary analysis of this raw data to produce nucleotide calls for each position of the sequence strand, along with quality scores that estimate the confidence in each nucleotide call. The large volume and random nature of the sequence reads produced by MPS instruments makes direct interpretation of this primary data by forensic or medical analysts impractical. Rather, secondary analysis of the sequence reads is necessary. The main method currently used for such secondary analysis is alignment of the sequence reads to one or more reference sequences, along with variant calling, where differences between the sequence reads and the reference sequence(s) are identified. This alignment produces a nucleotide-position-dependent signal and noise baseline, which can be visualized in the pileup presentation available in most alignment software. The x-axis of a read pileup is reference nucleotide position. Any given DNA reference nucleotide position can be represented in the sequence reads by five different primary analysis results (nucleotide states): A (adenine), C (cytosine), G (guanine), T (thymine), or N (unknown). As such, it is possible to express a noise baseline in aligned sequence reads by considering the reference nucleotide position as the dependent variable (x-axis) and the sums of nucleotide states at that position as the independent response variable.

According to one aspect, the present disclosure relates to methods of analyzing MPS data to determine MDLs for MPS-based workflows (which may then be used in secondary analysis of MPS data resulting from these MPS-based workflows). The presently disclosed methods express MPS data in a way that creates an intuitive categorization of signal and background noise and, further, allows background noise to be viewed in a manner consistent with a noise baseline. As such, these methods will allow forensic and/or medical analysts to perform secondary analysis of MPS data using familiar signal-to-noise-based considerations. In the presently disclosed methods, MPS instrument responses are expressed as a function of "unique nucleotide sequence." In accordance with International System of Units (SI) and International Union of Pure and Applied Chemistry (IUPAC) recommendations, the present disclosure treats "unique nucleotide sequence" as type of quantity (i.e., a measurable real property) having a dimension of one, consistent with its status as a counting quantity.

According to another aspect, the present disclosure also relates to methods of displaying MPS data that utilize MPS instrument responses being expressed as a function of "unique nucleotide sequence." In particular, the present disclosure proposes a new type of graphical display for MPS data in which the independent variable (typically represented on the ordinate or y-axis) is abundance count and the dependent variable (typically represented on the abscissa or x-axis) is unique nucleotide sequence. The present disclosure uses the term "kopiagram" to refer to such graphical displays. The kopiagram formats both signal and noise as counting quantities that are expressed on the same basis, allowing these quantities to be directly related and compared. The kopiagram also allows the expression of a proper noise baseline in which the unique nucleotide sequences are categorized. As a counted quantity, unique nucleotide sequence has no particular order of display. As such, unique nucleotide sequences can be presented in any desired order in a kopiagram (e.g., in order of decreasing/increasing abundance count, fragment length, lexographic order, random order, etc.).

Referring now to FIG. 1, one illustrative embodiment of a method 100 of analyzing MPS data is shown as a simplified flow diagram. In some embodiments, the method 100 may be implemented as one or more software routines executed by one or more processors. By way of example, it is contemplated that the method 100 may be performed by a processor of the MPS instrument analyzing the sample, in some embodiments, or by a processor of a separate computing device that receives nucleotide sequence data generated by the MPS instrument (for instance, in the form of a text-based computer file, such as a FASTA or FASTQ formatted file), in other embodiments. The method 100 is illustrated in FIG. 1 as a number of blocks 102-120, which will be described in detail below. It will be appreciated that, although the method 100 is generally shown in FIG. 1 and described below as having a linear workflow, the method 100 may be implemented using any number of workflows (including, by way of example, workflows in which various portions of the method 100 are performed in parallel).

The method 100 begins with block 102 in which a sample is sequenced using an MPS instrument to generate a number of text strings that each represent a nucleotide sequence read by the MPS instrument. By way of illustrative example, in some embodiments of block 102, a positive or negative control sample may be sequenced using the MPS instrument. Alternatively, block 102 may involve receiving a text-based computer file that contains a number of text strings that each represent a nucleotide sequence read by an MPS instrument. In either case, the text strings will each contain a number of characters that each represent a single nucleotide of a nucleotide sequence read by the MPS instrument. As noted above, due to the parallel nature of the MPS process, one sample may result in tens or hundreds of thousands of reads and, hence, associated text strings. Many MPS instruments output this data in files that follow either the FASTA or FASTQ format. As such, in some embodiments of the method 100, block 102 may involve receiving such a FASTA or FASTQ file and reading a number of text strings that each represent a nucleotide sequence from that file. In other embodiments, block 102 may involve receiving files in different formats (other than FASTA or FASTQ).

After block 102, the method 100 proceeds to block 104 in which a bioinformatic matching procedure is used to determine which reads from the MPS instrument (represented by the received text strings) correspond to one or more target loci present in the sample. In the illustrative embodiment of block 104, each of the received text strings is evaluated to determine whether it includes characters that represent a known flanking nucleotide sequence associated with a target locus. The nucleotide sequence of each target locus is generally flanked, on both the 5' and 3' ends, by particular flanking nucleotide sequences. These complex flanking nucleotide sequences can be rare or unique in the DNA analyzed by the MPS instrument. As such, the presence of one (or both) of these flanking nucleotide sequences may indicate the presence of a target locus in the nucleotide sequence represented by the text string. It is contemplated that, in other embodiments, the text strings may be searched for other specific nucleotide sequences (e.g., the forward or reverse primer binding sites used to PCR amplify each target locus). The presently disclosed methods may be applied to any molecular diagnostics application where specific target loci are being assayed (by way of illustrative example, forensic DNA analysis, medical diagnostics, and the like) and may be applied to any class of target locus, including, but not limited to, STR and SNP loci, mtDNA fragments used to determine haplotypes, and autosomal DNA haplotype fragments including microhap fragments.

The flanking nucleotide sequences, or other specific nucleotide sequences, used in block 104 may be any length. Longer sequences are more likely to be unique, but increasing length should be balanced against the slower bioinformatic processing inherent to long-sequence matching routines. Moreover, the longer a sequence, the more likely that reads which should contain the sequence will contain an error, reducing the sequence's value as an identifier. In some embodiments, block 104 may reference an external, updatable library of flanking nucleotide sequences (or other specific nucleotide sequences). The text string matching routine used in block 104 can be stringent (e.g., exact character matching) or flexible (e.g., close, overall matching). Block 104 may use any number of bioinformatic approaches, including, but not limited to, string matching routines built into common programming languages (e.g., Java, C++, Perl or Python), regular expression routines built into some programming languages (e.g., Perl) or available as modules for other programming languages, or the like. In some embodiments of block 104, each text string determined to correspond to a particular target locus may be grouped or segregated by locus. In other embodiments, each text string determined to correspond to a particular target locus may be tagged with specific metadata indicating this relationship. In some embodiments, text strings that are not identified as corresponding to a target locus (e.g., where the text string does not contain a known flanking nucleotide sequence associated with any of the target loci being assayed) may be discarded.

After block 104, the method 100 proceeds to block 106 in which the text strings representing nucleotide sequences associated with a particular target locus are selected for further processing. In other words, blocks 106-116 of the method 100 are generally performed on a locus-by-locus basis. As indicated in the illustrative embodiment of FIG. 1, blocks 106-116 may be repeated for multiple target loci identified as present in the sample in block 104. In some embodiments, block 106 may involve selecting a locus-specific list containing all of the text strings determined in block 104 to contain characters that represent a known flanking nucleotide sequence associated with a particular target locus. In other embodiments, block 106 may involve selecting all text strings that were tagged with specific metadata in block 104.

After block 106, the method 100 proceeds to block 108 in which each of the text strings selected in block 106 are trimmed to remove characters that do not represent the nucleotide sequence of interest. For instance, in some embodiments, all characters except those representing the particular target locus (e.g., the STR, the SNP, the mtDNA fragment, or other genetic marker) may be removed from each of the selected text strings. It will be appreciated that, where the target locus is an SNP, the text strings may each contain only a single text character (representing a single nucleotide) after block 108. In the illustrative embodiment, the characters representing the 5' and 3' flanking nucleotide sequences (used to identify the text string in block 104), as well as any characters outside of the characters representing the 5' and 3' flanking nucleotide sequences, are removed from each of the selected text strings in block 108. However, the selected text strings remain identified with the particular target locus due to the grouping, metadata tagging, or other segregation procedure performed in block 104. It is contemplated that, in some embodiments of the method 100, block 108 may be omitted where all characters in the selected text strings represent the nucleotide sequence of interest.

After block 108, the method 100 proceeds to block 110 in which the unique text strings included in the selected text strings (associated with a particular target locus) are grouped and counted. In other words, block 110 determines an abundance count for each unique nucleotide sequence represented by the selected text strings. In the illustrative embodiment, block 110 involves comparing the selected text strings to one another to determine each unique text string and its abundance within the group of selected text strings. Block 110 may be performed by applying a stringent text string matching routine (e.g., exact character matching) to the selected text strings. As noted above, it is contemplated that string matching routines built into common programming languages (e.g., Java, C++, Perl or Python), regular expression routines built into some programming languages (e.g., Perl) or available as modules for other programming languages, or the like, may be used. Block 110 may also involve sorting the unique text strings, each representing a unique nucleotide sequence read by the MPS instrument, into a list according to their abundance counts. FIG. 2 illustrates top and bottom portions of such a list, in which the hundreds of unique nucleotide sequences output by an MPS instrument and determined to be associated with the D3S1358 locus were sorted by abundance count. FIG. 3 illustrates similar lists for two SNP loci. In particular, the unique nucleotide sequences output by an MPS instrument and determined to be associated with the rs1805007 and rs1681982 loci, respectively, have been sorted by abundance count in FIG. 3. It will be appreciated that the exact-matching scheme used in block 110 will result in an abundance count (i.e., a number of occurrences) for each even slightly different nucleotide sequence.

After block 110, the method 100 proceeds to block 112 in which the unique text strings representing noise responses are identified from among the selected text strings. It is contemplated that the unique text strings representing noise responses may be identified in block 112 in any number of ways. For instance, in some embodiments, the sample may be a known standard with a known informative signal profile that can be removed, leaving only the noise responses. As one illustrative example, the method 100 might be used to analyze a known standard having a genotype of alleles sized 10 and 14 at a given locus. In this example, block 112 may involve removing or ignoring the unique text strings representing size 10 and 14 alleles (and, optionally, stutter artifacts of those alleles) and identifying all of the remaining unique text strings as representing noise responses.

In other illustrative embodiments, block 112 may involve block 114 in which the unique text strings representing the "true" allele(s) are identified from among the selected text strings. As noted above, while the MPS workflow results in many unique nucleotide sequences for a particular target locus, only one or two of these nucleotide sequences will be the "true" alleles for that particular target locus (in the case of a sample from one human). Block 114 may involve an allelotyping algorithm used to identify the unique text strings representing the "true" allele(s) based on the abundance counts determined in block 110. For instance, in some embodiments, any of the allelotyping methods described in U.S. patent application Ser. No. 13/952,761 (filed Jul. 29, 2013, and entitled "Allelotyping Methods for Massively Parallel Sequencing") may be used to identify the unique text strings representing the "true" allele(s) for the target locus. In embodiments of block 112 that include block 114, identification of the unique text strings representing "true" allele(s) may be performed prior to identification of the unique text strings representing noise responses, to ensure that the "true" alleles are not identified as noise responses. In some illustrative embodiments, block 112 may involve identifying all unique text strings determined not to represent a "true" allele as instead representing a noise response.

In still other illustrative embodiments, block 112 may also involve block 116 (in addition to block 114) in which the unique text strings representing artifacts are identified from among the selected text strings. As noted above, depending on the particular processes used, the MPS workflow may result in several unique nucleotide sequences that represent instrument- and/or method-specific artifacts (e.g., stutter artifacts resulting from strand slippage during PCR). Block 116 may involve an allelotyping algorithm used to identify the unique text strings representing such artifacts based on the abundance counts determined in block 110. For instance, in some embodiments, any of the allelotyping methods described in U.S. patent application Ser. No. 13/952,761 (filed Jul. 29, 2013, and entitled "Allelotyping Methods for Massively Parallel Sequencing") may be used to identify the unique text strings representing artifacts. In embodiments of block 112 that include blocks 114, 116, identification of the unique text strings representing "true" allele(s) and artifacts may be performed prior to identification of the unique text strings representing noise responses, to ensure that the "true" alleles and artifacts are not identified as noise responses. In some illustrative embodiments, block 112 may involve identifying all unique text strings determined not to represent either a "true" allele or an artifact as instead representing a noise response.

After block 112, the method 100 may optionally return to block 106 in which the text strings representing nucleotide sequences associated with another particular target locus are selected for processing in blocks 106-116 in the same manner described above. In particular, where multiple target loci are identified as present in the sample in block 104, the method 100 may involve performing the blocks 106-116 for each of the target loci (in either an iterative or parallel fashion). As such, it is contemplated that block 118 (determining an MDL) and block 120 (outputting a graphical display), both further described below, may each be based upon the results of blocks 106-116 for a single target locus or multiple target loci, in various embodiments of the method 100. Moreover, it is also contemplated that blocks 118, 120 may each be based upon the results of blocks 106-116 from any number of samples or tests.

After block 112, the illustrative embodiment of method 100 proceeds to block 118 in which an MDL is determined as function of the abundance counts determined in block 110 for the unique text strings identified as representing noise responses in block 112. It is contemplated that the MDL may be determined in block 118 by any number of methods using the abundance counts associated with the noise responses. For instance, any of the approaches or techniques described above for determining an MDL associated with an analytical method may be applied in block 118. In some embodiments, block 118 may involve applying a form of Equation (5) to the abundance counts associated with the noise responses (e.g., the MDL may be calculated by subtracting the smallest abundance count associated with a noise response from the largest abundance count associated with a noise response and multiplying that difference by two). In other embodiments, block 118 may involve applying a form of Equation (6) to the abundance counts associated with the noise responses (e.g., the MDL may be calculated by multiplying the standard deviation of the abundance counts associated with the noise responses by a constant and adding that product to the mean of the abundance counts associated with the noise responses). As noted above, the abundance counts used in determining the MDL in block 118 may be associated with noise responses corresponding to one or more target loci, one or more samples, and/or one or more tests.

After block 118, the illustrative embodiment of method 100 proceeds to block 120 in which a graphical display representing the one or more target loci (corresponding to the text strings selected in one or more iterations of block 106) is output. It will be appreciated that, in some illustrative embodiments, "outputting the graphical display" may involve outputting electronic signals containing data necessary to cause a display device (local or remote) to render the graphical display. It is contemplated that the graphical display output in block 120 may take any number of forms. Generally described, however, this graphical display will comprise a plurality of graphical elements that each correspond to one of the unique text strings for which an abundance count was determined in block 110 and that each graphically represent that abundance count. As compared to CE-based workflows, the data derived from MPS-based workflows is of a fundamentally different form. Whereas CE-based analysis reports the sizes (lengths) of the target PCR amplicons (which are aggregated by size, regardless of nucleotide sequence), MPS-based analysis reports the actual nucleotide sequences of the target PCR amplicons. The presently disclosed "kopiagrams" take account of this fundamental difference by organizing the data by unique nucleotide sequence. In the illustrative embodiment of the method 100, block 120 involves the output of such a kopiagram, examples of which are shown in FIGS. 4-7 (further described below).

Figure 4:
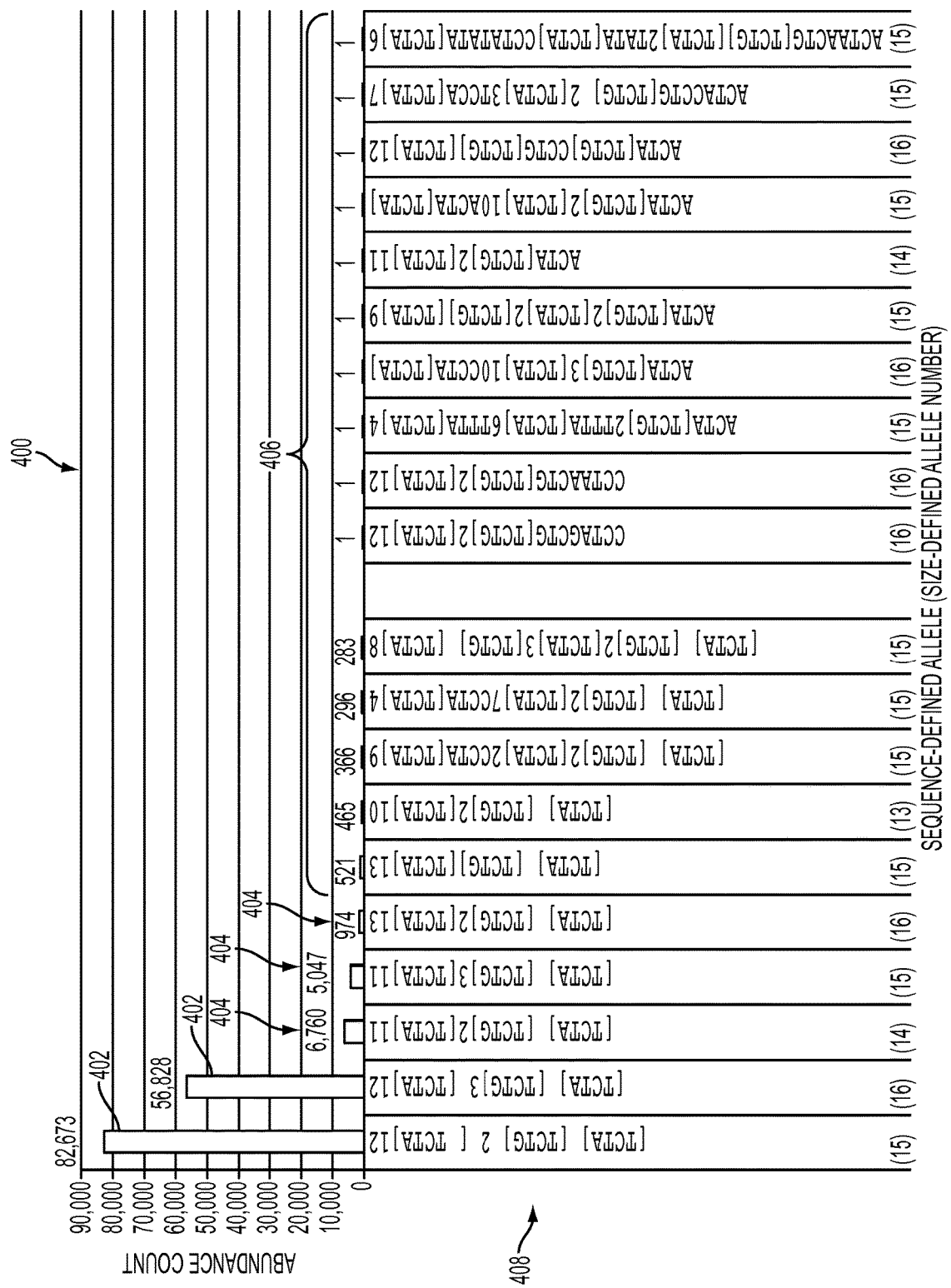
FIG. 4 is one illustrative embodiment of a kopiagram, representing the abundance counts of the unique text strings from FIG. 2 (including two true alleles, three stutter artifacts, and fifteen noise responses obtained from MPS of the D3S1358 locus) (FIG. 4 discloses SEQ ID NOS 1-20, respectively, in order of appearance)

One illustrative example of a kopiagram 400 is shown in FIG. 4. The kopiagram 400 graphically represents the exemplary data contained in FIG. 2. The kopiagram 400 is illustratively embodied as a bar graph that includes a plurality of bars 402-406. Each of the bars 402-406 corresponds to a unique text string (included in the text strings selected in block 106 as corresponding to the D3S1358 locus). In particular, the bars 402-406 correspond to the ten unique text strings (representing ten unique nucleotide sequences) that were determined to have the ten highest abundance counts in block 110 and to ten additional unique text strings (representing another ten unique nucleotide sequences) that appear as singletons in the data set. Bars 402 correspond to the two "true" alleles for the particular locus represented by the kopiagram 400 (i.e., D3S1358). Bars 404 each correspond to a stutter artifact of one of the "true" alleles. Bars 406 each correspond to a sequencing error of one of the "true" alleles. For example, the eleventh bar in the chart displays a T to C substitution in the first nucleotide position and a T to G substitution in the fifth nucleotide position. In the embodiment of FIG. 4, bars 404-406 may each be considered represent a noise response. While the kopiagram 400 includes eighteen noise responses, other embodiments of the kopiagram may display more or less noise responses. In some illustrative embodiments, the number of noise responses included in the kopiagram may be configurable by a user.

Each of the bars 402-406 of the kopiagram 400 has a height that is indicative of the abundance count (determined in block 110) for the unique text string that is represented by that bar 402-406. As such, the y-axis of the kopiagram 400 includes indicia representing various abundance counts and may be used to quantify signal response. The x-axis of the kopiagram 400 includes a series of labels 408 (each label 408 being associated with one of the bars 402-406). In the illustrative embodiment, the labels 408 each designate the unique nucleotide sequence represented by the unique text string that corresponds to one of the bars 402-406. In particular, in the illustrative embodiment, the labels 408 include categorical designations using the International Society for Forensic Genetics (ISFG) convention for allele designations. In the illustrative embodiment, the labels 408 further include a size-defined allele number (in parentheses). As suggested above, the bars 402-206 (and the associated labels 408) of the kopiagram 400 may be arranged in any desired order. In the illustrative embodiment shown in FIG. 4, the bars 402-406 are arranged in order of decreasing abundance count for the corresponding unique text strings/nucleotide sequences (from left to right).

Figure 5:
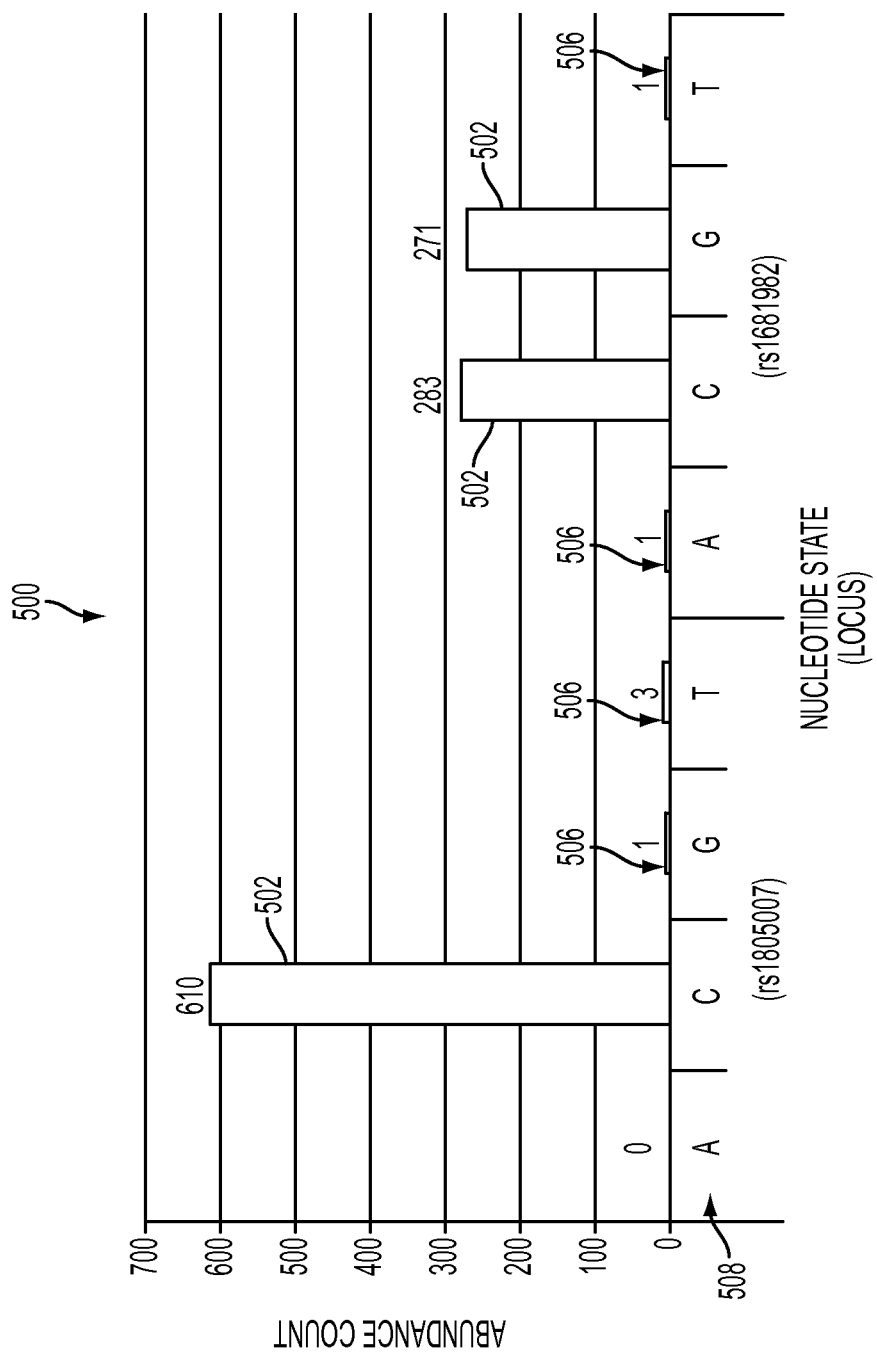
FIG. 5 is another illustrative embodiment of a kopiagram, representing the abundance counts of the unique text strings from FIG. 3 (including one true allele and two noise responses obtained from MPS of the rs1805007 locus and including two true alleles and two noise responses obtained from MPS of the rs1681982 locus)

Another illustrative example of a kopiagram 500 is shown in FIG. 5. The kopiagram 500 graphically represents the exemplary data contained in FIG. 3. Like the kopiagram 400, the kopiagram 500 is illustratively embodied as a bar graph that includes a plurality of bars 502, 506. Each of the bars 502, 506 corresponds to a unique text string (included in the text strings selected in block 106 as corresponding to either the rs1805007 locus or the rs1681982 locus). In particular, the bars 502, 506 correspond to the seven unique text strings (representing seven unique nucleotide sequences or states) that were determined to have non-zero abundance counts in block 110. Bars 502 correspond to the "true" alleles for the two target loci represented by the kopiagram 400, while bars 506 each correspond to a sequencing error of one of these "true" alleles. The kopiagram 500 has other similar features to the kopiagram 400 discussed above (e.g., the labels 508).

Figure 6:
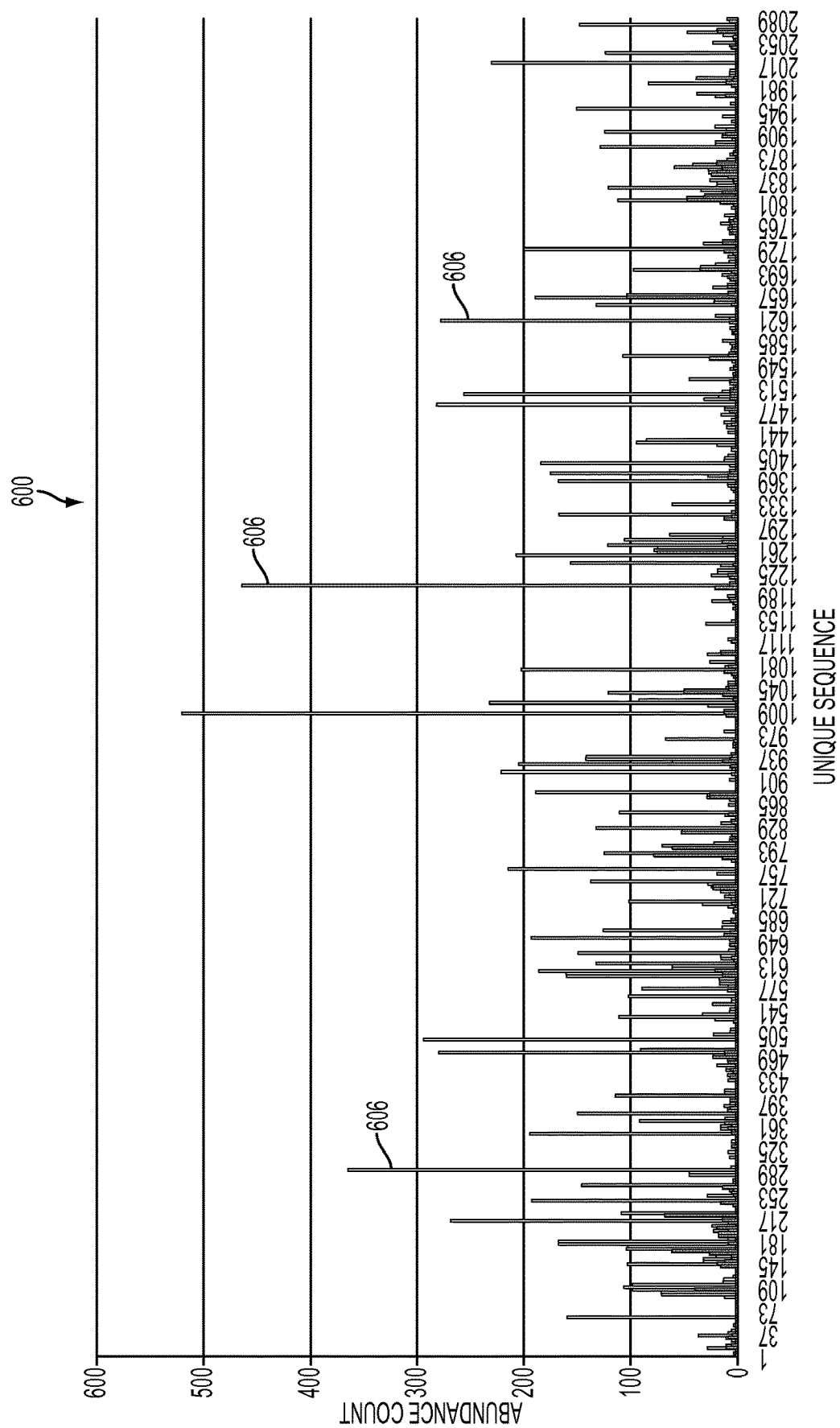
FIG. 6 is yet another illustrative embodiment of a kopiagram, representing the abundance counts of a full set of noise responses (in this case, excluding both the two true alleles and the three stutter artifacts) obtained from MPS of the D3S1358 locus.

Further illustrative examples of kopiagrams 600, 700 are shown in FIGS. 6-7, respectively. The kopiagrams 600, 700 each include a plurality of bars 606, 706 (only a few of which are labeled in FIGS. 6-7) that represent the abundance counts of a full set of noise responses but do not include any graphical elements corresponding to "true" alleles or stutter artifacts. Each of the bars 606, 706 corresponds to a unique text string (included in the text strings selected in block 106 as corresponding to a particular target locus) that was identified as representing a noise response (in block 112). The kopiagrams 600, 700, as shown in FIGS. 6-7, may serve as a mechanism for visualizing the noise baseline. By categorizing noise responses in terms of unique nucleotide sequence, the noise responses are on the same "scale" as the signal (i.e., the "true" allele(s), which are also defined by unique nucleotide sequence). By contrast, other current systems (e.g., reference alignment-based systems) for typing alleles do not have a natural noise measure at the allele level.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A method comprising:
amplifying nucleotide sequences in a sample using a PCR amplification process to produce an amplified sample;
using a massively parallel sequencing (MPS) instrument to read the nucleotide sequences of the amplified sample and generate a first plurality of text strings based on the amplified sample, wherein the first plurality of text strings comprises at least ten thousand text strings;
selecting, with a processor, a second plurality of text strings from the first plurality of text strings generated by the MPS instrument, wherein each of the selected second plurality of text strings represents a nucleotide sequence that corresponds to a first target locus in the amplified sample;
comparing, with the processor, the selected second plurality of text strings to one another to determine an abundance count for each unique text string included in the selected second plurality of text strings;
identifying, with the processor, a first number of unique text strings included in the selected second plurality of text strings as representing noise responses; and
determining, with the processor, a method detection limit (MDL) as a function of the abundance counts for the first number of unique text strings identified as representing noise responses.

2. The method of claim 1, further comprising identifying, with the processor, one or more unique text strings included in the selected second plurality of text strings as representing one or more true alleles for the first target locus;
wherein the first number of unique text strings identified as representing noise responses includes all of the unique text strings included in the selected second plurality of text strings that were not identified as representing the one or more true alleles for the first target locus.

3. The method of claim 2, wherein identifying one or more unique text strings as representing the one or more true alleles for the first target locus comprises identifying a unique text string that represents either a short tandem repeat (STR) or a single nucleotide polymorphism (SNP).

4. The method of claim 1, further comprising:
identifying, with the processor, one or more unique text strings included in the selected second plurality of text strings as representing one or more true alleles for the first target locus;
identifying, with the processor, one or more unique text strings included in the selected second plurality of text strings as each representing an artifact;
wherein the first number of unique text strings identified as representing noise responses includes all of the unique text strings included in the selected second plurality of text strings that were not identified as representing either the one or more true alleles for the first target locus or an artifact.

5. The method of claim 4, wherein:
identifying one or more unique text strings as representing the one or more true alleles for the first target locus comprises identifying a unique text string that represents a short tandem repeat (STR); and
identifying one or more unique text strings as representing an artifact comprises identifying a unique text string that represents a stutter artifact of the STR.

6. The method of claim 1, wherein determining the MDL comprises doubling a difference between (i) a largest abundance count for the first number of unique text strings identified as representing noise responses and (ii) a smallest abundance count for the first number of unique text strings identified as representing noise responses.

7. The method of claim 1, wherein determining the MDL comprises calculating a product of (i) a constant and (ii) a standard deviation of the abundance counts for the first number of unique text strings identified as representing noise responses.

8. The method of claim 7, wherein determining the MDL further comprises adding a mean of the abundance counts for the first number of unique text strings identified as representing noise responses to the product.

9. The method of claim 1, wherein determining the MDL comprises calculating a ratio between (i) a mean of the abundance counts for the first number of unique text strings identified as representing noise responses and (ii) a standard deviation of the abundance counts for the first number of unique text strings identified as representing noise responses.

10. The method of claim 1, further comprising:
selecting, with the processor, a third plurality of text strings from the first plurality of text strings generated by the MPS instrument, wherein each of the selected third plurality of text strings represents a nucleotide sequence that corresponds to a second target locus in the amplified sample;

comparing, with the processor, the selected third plurality of text strings to one another to determine an abundance count for each unique text string included in the selected third plurality of text strings; and identifying, with the processor, a second number of unique text strings included in the selected third plurality of text strings as representing noise responses;

wherein, with the processor, determining the MDL comprises determining the MDL as a function of both the abundance counts for the first number of unique text strings identified as representing noise responses and the abundance counts for the second number of unique text strings identified as representing noise responses.

11. The method of claim 10, wherein the second plurality of text strings comprises at least ten thousand text strings.

12. The method of claim 1, wherein the second plurality of text strings comprises at least ten thousand text strings.

13. A method comprising:

amplifying nucleotide sequences in a sample using a PCR amplification process to produce an amplified sample;

using a massively parallel sequencing (MPS) instrument to read the nucleotide sequences of the amplified sample and generate a first plurality of text strings based on the amplified sample, wherein the first plurality of text strings comprises at least ten thousand text strings;

selecting, with a processor, a second plurality of text strings from the first plurality of text strings generated by the MPS instrument, wherein each of the selected first plurality of text strings represents a nucleotide sequence that corresponds to a first target locus in the amplified sample;

comparing, with the processor, the selected second plurality of text strings to one another to determine an abundance count for each unique text string included in the selected second plurality of text strings; and outputting a graphical display, wherein the graphical display comprises a first plurality of graphical elements that each correspond to one of the unique text strings included in the selected second plurality of text strings and that each represent the abundance count determined for the corresponding unique text string.

14. The method of claim 13, wherein the graphical display is a bar graph comprising a plurality of bars that each correspond to one of the unique text strings included in the selected second plurality of text strings, each of the plurality of bars having a height indicative of the abundance count determined for the corresponding unique text string.

15. The method of claim 14, wherein the bar graph further comprises a label associated with each of the plurality of bars, each label designating the nucleotide sequence represented by the corresponding unique text string.

16. The method of claim 14, wherein the plurality of bars comprise one or more bars that each represent a true allele for the first target locus.

17. The method of claim 16, wherein the plurality of bars are arranged in order of decreasing height.

18. The method of claim 14, wherein the plurality of bars represent a full set of noise responses for the first target locus.

19. The method of claim 18, wherein the plurality of bars are arranged in a random order.

20. The method of claim 13, further comprising:

selecting, with the processor, a third plurality of text strings from the first plurality of text strings generated by the MPS instrument, wherein each of the selected third plurality of text strings corresponds to a second target locus in the amplified sample; and comparing, with the processor, the selected third plurality of text strings to one another to determine an abundance count for each unique text string included in the selected third plurality of text strings;

wherein the graphical display further comprises a second plurality of graphical elements that each correspond to one of the unique text strings included in the selected third plurality of text strings and that each represent the abundance count determined for the corresponding unique text string.

* * * * *